US012320806B2

United States Patent
Harding et al.

(10) Patent No.: US 12,320,806 B2
(45) Date of Patent: Jun. 3, 2025

(54) ASSAY FOR FREE LIGHT CHAINS

(71) Applicant: THE BINDING SITE GROUP LIMITED, Birmingham (GB)

(72) Inventors: Stephen Harding, Birmingham (GB); Jamie Ashby, Birmingham (GB)

(73) Assignee: THE BINDING SITE GROUP LIMITED, Birmingham (GB)

( * ) Notice: Subject to any disclaimer, the term of this patent is extended or adjusted under 35 U.S.C. 154(b) by 975 days.

(21) Appl. No.: 16/079,173

(22) PCT Filed: Feb. 24, 2017

(86) PCT No.: PCT/GB2017/050485
§ 371 (c)(1),
(2) Date: Aug. 23, 2018

(87) PCT Pub. No.: WO2017/144896
PCT Pub. Date: Aug. 31, 2017

(65) Prior Publication Data
US 2019/0056388 A1 Feb. 21, 2019

(30) Foreign Application Priority Data
Feb. 26, 2016 (GB) .................................. 1603359

(51) Int. Cl.
*G01N 33/563* (2006.01)
*G01N 33/543* (2006.01)
*G01N 33/68* (2006.01)

(52) U.S. Cl.
CPC ..... *G01N 33/563* (2013.01); *G01N 33/54306* (2013.01); *G01N 33/6857* (2013.01)

(58) Field of Classification Search
CPC .......................... G01N 33/563; G01N 33/6857
See application file for complete search history.

(56) References Cited

U.S. PATENT DOCUMENTS

| | | | | |
|---|---|---|---|---|
| 4,791,068 A * | 12/1988 | Loskutoff | ............ | C07K 14/005 435/13 |
| 2002/0168376 A1 * | 11/2002 | Babich | ................. | C07K 14/415 424/185.1 |
| 2007/0065891 A1 * | 3/2007 | Ebinuma | ................ | G01N 33/74 435/7.31 |
| 2009/0123946 A1 * | 5/2009 | Birkenmeyer | ..... | G01N 33/6893 435/7.21 |
| 2011/0129815 A1 * | 6/2011 | Yamagaito | ......... | G01N 33/5767 435/5 |
| 2011/0130305 A1 * | 6/2011 | Patton | ................ | G01N 33/6845 506/15 |
| 2011/0294700 A1 * | 12/2011 | Thelen | ............... | G01N 33/6848 506/12 |
| 2012/0220052 A1 * | 8/2012 | Mead | ................. | G01N 33/6857 436/501 |
| 2013/0071855 A1 * | 3/2013 | Bradwell | ........... | G01N 33/6893 435/7.4 |
| 2013/0217149 A1 * | 8/2013 | Mead | ............... | G01N 33/54313 436/501 |
| 2014/0194383 A1 * | 7/2014 | Barany | ................... | A61P 11/00 514/64 |
| 2018/0042995 A1 * | 2/2018 | Weissbrich | ............... | C07F 9/50 |

FOREIGN PATENT DOCUMENTS

| | | |
|---|---|---|
| WO | 2011/021041 A2 | 2/2011 |
| WO | 2012/010881 A1 | 1/2012 |

OTHER PUBLICATIONS

Falconar et al. "Immunoaffinity purification of native dimer forms of the flavivirus non-structural glycoprotein, NS 1", Journal of Virological Methods. 30 (1990) 323-332 (Year: 1990).*
USP 35-NF 30, "Immunological Test Methods", Section 1103, Second Supplement, Apr. 2012, pp. 5678-5686 (Year: 2012).*
Tate, J., et al. "Quantitative Serum Free Light Chain Assay—Analytical Issues," Clin Biochem Rev, vol. 30, 2009, pp. 131-140.
Li, C., et al. "Influence of Immunoglobulin Light Chain Dimers on the Results of the Quantitative Nephelometric Assay," Clin. Lab, vol. 57, 2011, pp. 53-57.
Abraham, R.S., et al. "Trimolecular Complexes of λ Light Chain Dimers in Serum of a Patient with Multiple Myeloma," Clinical Chemistry, 48:10, 2002, pp. 1805-1811.
Katzmann, J.A., et al. "Serum Reference Intervals and Diagnostic Ranges for Free κ and Free λ Immunoglobulin Light Chains: Relative Sensitivity for Detection of Monoclonal Light Chains," Clinical Chemistry 48:9, 2002, pp. 1437-1444.
Lock, R.J., et al. "A multicentre study comparing two methods for serum free light chain analysis," Annals of Clinical Biochemistry, vol. 50, 2013, pp. 255-261.
Mead, G.P., et al. "Overestimation of Serum κ Free Light Chain Concentration by Immunonephelometry," Clinical Chemistry 56:9, 2010, pp. 1503-1504.
Schnebelen, A., et al. "Alleviation of IgM Monoclonal Protein Interference in Nephelometric Assays by Sample Treatment With Reducing Agent in a Chaotropic Salt Solution," Am J Clin Pathol, vol. 137, 2012, pp. 26-28.
Briand, P-Y, et al. "Analytical performance of the serum free light chain assay," Clin Chem Lab Med 48(1), 2010, pp. 73-79.

(Continued)

*Primary Examiner* — Gailene Gabel
(74) *Attorney, Agent, or Firm* — Stites & Harbison, PLLC; Mandy Wilson Decker; Patrick M. Torre

(57) ABSTRACT

The application describes a method of quantifying a multimeric analyte in a sample comprising: (i) treating the multimeric analyte with a separating agent selected to convert at least a portion of the multimeric analyte into monomeric analyte; (ii) binding the analyte to an analyte-specific binding agent; (iii) comparing the amount of binding of the analyte to the analyte-specific binding agent to a calibration curve, wherein the calibration curve is obtained (i) by binding the analyte-specific binding agent to one or more predetermined amounts of separating agent treated analyte, prior to contacting with analyte-specific binding agent or (ii) by binding the analyte-specific binding agent to a predetermined amount of substantially monomeric analyte; and (iv) determining an amount of the multimeric analyte in the sample.

20 Claims, 7 Drawing Sheets

(56) References Cited

OTHER PUBLICATIONS

European Patent Office, International Search Report issued in corresponding Application No. PCT/GB2017/050485, dated May 5, 2017.
Barnidge, D.R., et al. "Monitoring free light chains in serum using mass spectrometry," Clin Chem Lab Med 2016: 54(6): 1073-1083.
Drayson, M., et al. "Serum free light-chain measurements for identifying and monitoring patients with nonsecretory multiple myeloma," Blood, May 1, 2001, vol. 97, No. 9, pp. 2900-2902.
Faint, J.M., et al. "Quantification of polyclonal free light chains in clinical samples using a single turbidimetric immunoassay," Clin Chem Lab Med 2014: 52(11): 1605-1613.
Tietsch De Moraes Hungria, V., et al. "Serum free light chain assays not total light chain assays are the standard of care to assess Monoclonal Gammopathies," Rev Bras Hematol Hemoter, 2016; 38(1); 37-43.
Wall, J., et al. "Thermodynamic Instability of Human λ6 Light Chains: Correlation with Fibrillogenicity," Biochemistry 1999, 38, 14101-14108.

\* cited by examiner

ASSAY FOR FREE LIGHT CHAINS

The invention relates to methods of quantifying a multimeric analyte such as antibody free light chains in a sample by converting the multimeric analyte into monomeric analyte. Kits for carrying out the method and antibodies raised against separated monomeric analytes are also provided.

The Applicants have for many years studied free light chains as a way of assaying for a wide-range of monoclonal gammopathies in patients. The use of such free light chains in diagnosis is reviewed in detail in the book "Serum Free Light Chain Analysis, Sixth Edition (2010) A. R. Bradwell et al, ISBN 9780704427969".

Antibodies comprise heavy chains and light chains. They usually have a two-fold symmetry and are composed of two identical heavy chains and two identical light chains, each containing variable and constant region domains. The variable domains of each light-chain/heavy-chain pair combine to form an antigen-binding site, so that both chains contribute to the antigen-binding specificity of the antibody molecule. Light chains are of two types, κ and λ and any given antibody molecule is produced with either light chain but never both. There are approximately twice as many κ as λ molecules produced in humans, but this is different in some mammals. Usually the light chains are attached to heavy chains. However, some unattached "free light chains" are detectable in the serum or urine of individuals. Free light chains may be specifically identified by raising antibodies against the surface of the free light chain that is normally hidden by the binding of the light chain to the heavy chain. In free light chains (FLC) this surface is exposed, allowing it to be detected immunologically. Commercially available kits for the detection of κ or λ free light chains include, for example, "Freelite™", manufactured by The Binding Site Limited, Birmingham, United Kingdom. The Applicants have previously identified that measuring the amount of free κ, free λ and/or free κ/free λ ratios, allows the detection and monitoring of monoclonal gammopathies in patients. It has been used, for example, as an aid in the diagnosis of intact immunoglobulin multiple myeloma (MM), light chain MM, non-secretory MM, AL amyloidosis, light chain deposition disease, smouldering MM, plasmacytoma and MGUS (monoclonal gammopathies of undetermined significance). Detection of FLC has also been used, for example, as an aid to the diagnosis of other B-cell dyscrasia and indeed as an alternative to urinary Bence Jones protein analysis for the diagnosis of monoclonal gammopathies in general.

Conventionally, an increase in one of the λ or κ light chains is looked for. For example, multiple myelomas result from the monoclonal multiplication of a malignant plasma cell, resulting in an increase in a single type of cell producing a single type of immunoglobulin. This results in an increase in the amount of free light chain, either λ or κ, observed within an individual. This increase in concentration may be determined, and usually the ratio of the free κ to free λ is determined and compared with the normal range. This aids in the diagnosis of monoclonal disease. Moreover the free light chain assays may also be used for the following of treatment of the disease in patients. Prognosis of, for example, patients after treatment for AL amyloidosis may be carried out. Furthermore, free light chain assays may be used in the risk stratification and associated patient management, for example, the risk of transformation from MGUS to multiple myeloma.

Katzman et al (Clin. Chem. (2002); 48(9): 1437-1944) discuss serum reference intervals and diagnostic ranges for free κ and free λ immunoglobulins in the diagnosis of monoclonal gammopathies. Individuals from 21-90 years of age were studied by immunoassay and compared to results obtained by immunofixation to optimise the immunoassay for the detection of monoclonal free light chains (FLC) in individuals with B-cell dyscrasia.

The amount of κ and λ FLC and the κ/λ, ratios were recorded allowing a reference interval to be determined for the detection of B-cell dyscrasias.

The Applicants have also identified that assaying for FLC and especially total FLC can be used to predict long-term survival of individuals, even when the individual is an apparently healthy subject. They have found that FLC concentration is statistically, significantly linked to long-term survival. Moreover, this link appears to be similar or better than the link for existing long-term survival prognostic markers such as cholesterol, creatinine, cystatin C and C-reactive protein. This is the subject of WO 2011/021041A.

A problem with many assays for free light chains (FLC) is that the free light chains often exist in polymeric forms in blood, serum, plasma and urine, for example, dimers, tetramers or higher polymeric forms. This can result in some limitations of the prior art assays. However, other techniques such as using gel electrophoresis, for example, can lead to underestimation of the monoclonal FLC as variable sized polymers may not run as a clear band. For FLC nephelometric and turbidimetric assays the presence of polymerised FLCs may enhance the reaction and lead to an overestimation in comparison to a calibrator which does not have highly polymerised FLCs.

Schebelen A. et al (Am. J. Clin. Pathol. (2012), 137, 26-28) describes a problem associated with some monoclonal IgM proteins interfering with the detection of IgA and IgG by nephelometry. The IgM complexes were broken up using β-mercaptoethanol. This produced a 50% drop in IgG and IgA concentrations observed, while IgM concentrations were unchanged. This was consistent with dissociation of IgM complexes, reducing light scattering by IgM complexes in IgA and IgG nephelometric reactions.

Mead G. P. and Can-Smith H. G. (Clin. Chem (2010) 56, 9) discuss the overestimation of serum κ FLC by immunonephelometry. In Mead and Carr-Smith, the authors noted the observation was more prevalent with κ than λ FLC and believed it to be due to the presence of high molecular weight κ polymers. The authors concluded that nephelometric inaccuracies due to polymerisation would be minimised when monoclonal FLC production was low and that when polymerisation did occur, densitometric measurements from alternative electrophoresis gels would be less accurate because of higher background levels of polyclonal FLCs. Although infrequent, there are reported examples of higher molecular weight lambda polymers. Abraham ((Clin Chem (2002) 48, 10) discuss aggregates, greater than tetramers, of a lambda monoclonal protein. Briand (Clin Chem Lab Med, 2010) comment on the overestimation of lambda concentration on a sample from a patient being monitored for multiple myeloma.

Li C. et al (Clin. Lab (2011) 57, 53-57) also discussed the influence of FLC dimers on quantitative nephelometric assay, when measuring FLCs in urine. Samples with urinary κ and λ FLC were treated with 1% vol/vol (143 mM) β-mercaptoethanol (2-ME) to produce monomeric forms. The authors reported that light chain dimers combined with more antibodies producing elevated results compared to FLC monomers. The results were variable between different patients with multiple myeloma (MM) although where a change was reported by Li et al the untreated sample always showed an elevation. In contrast, Mead and Carr-Smith (Supra) report that in some cases the polymerisation of the FLC could reduce the epitopes available for binding to anti-FLC antibodies and in other cases that the repeating epitopes in polymeric FLCs may enhance the immune complex reaction. This shift in the reported value would depend on the individual monoclonal free light chain being measured.

Urinary FLC does not contain intact immunoglobulin. However, had the authors looked at serum samples, using the extreme concentrations of 2-ME, it could be anticipated that this would have resulted in the release of further light chains from intact immunoglobulins in the serum due to reduction of the disulphide bonds linking the light chains to the heavy chains. Additionally, it would be expected that disulphide bonds within each monomer would be reduced and the monomer damaged. Moreover, the authors failed to derive FLC values using calibrators which had also been treated with a reducing agent, thus were not comparing equivalent immuno reactions. The effect of the 2-ME on the anti-FLC antibody was also not studied. The concentrations of 2-ME used would be expected to break the intact antibody.

The inventors have realised that being able to separate the multimeric free light chains would improve the accuracy of the assays, especially when the calibrator is itself also treated in the same way, so that a constant approach is being taken to both the sample and the calibrator.

The applicant has also recognised that in many cases, the prior art assays used antibodies or fragments of antibodies to detect the presence of the free light chains. This leads to potential problems because many of the reagents that could be used to separate the monomeric free light chain are also likely to effect the binding of, for example, light chain to the heavy chains of intact immunoglobulins such as the antibodies used to detect the free light chain, or indeed the immunoglobulins in the sample where, for example, the sample is a serum sample. This would lead to false or inaccurate results. For example, where the reducing agent is β-mercaptoethanol (2-ME) that reducing agent is known to break the disulphide bonds between the light chain and heavy chain and indeed between the two heavy chains of the typical antibody if high enough concentrations are used.

The applicant has found that it is possible to selectively separate the multimeric free light chains without substantially damaging the antibodies used in the assay or indeed substantially damaging intact immunoglobulins when present. Additionally, they have also found that it is possible to quench the separating reaction prior to adding the antibody or fragments.

That discovery could also be applied to other multimeric analytes.

The invention therefore provides:

A method of quantifying a multimeric analyte in a sample comprising:
(i) treating the multimeric analyte with a separating agent selected to convert at least a portion of the multimeric analyte into monomeric analyte;
(ii) binding the analyte to an analyte-specific binding agent;
(iii) comparing the amount of binding of the analyte to the analyte-specific binding agent to a calibration curve, wherein the calibration curve is obtained by binding the analyte-specific binding agent to a predetermined amount of separating agent treated analyte, prior to contacting with analyte-specific binding agent; and
(iv) determining an amount of the multimeric analyte in the sample.

The invention also provides a method of quantifying a multimeric analyte in a sample comprising:
(i) treating the multimeric analyte with a separating agent selected to convert at least a portion of the multimeric analyte into monomeric analyte; and
(ii) binding the analyte to an analyte-specific antibody, or fragment thereof, wherein the concentration of the separating agent is selected to not substantially affect the analyte specific antibody or fragment and is typically less than 100 mM, less than 50 mM, less than 30 mM or less than 20 mM and optionally greater than 1 mM or greater than 5 mM.

The methods of the invention typically quantitatively quantify the analyte.

The analyte-specific binding agent is typically an antibody or an analyte-specific fragment thereof, such as a Fab, Fab', F(ab')$_2$ or Fv fragment. The antibody may be a monoclonal antibody or may be a polyclonal antibody. It may be a single domain antibody. The analyte-specific binding agent may also be an aptamer.

Typically the separating agent is incubated with the sample for between 5 seconds to 20 minutes, especially 30 seconds and 5 minutes prior to quenching or adding the FLC binding agent.

Typically the multimeric analyte is a free light chain (FLC). The free light chain may be λ, κ or may be total FLC. Total FLC means the amount of κ and λ free light chains in the sample from the subject. These may be detected separately by separate assays, such as the Freelite™ assay available commercially from The Binding Site Group Limited, Birmingham, United Kingdom, or alternatively by a single assay such as the Combylite™ assay which is also available commercially from The Binding Site Group Limited, Birmingham, United Kingdom and which is the subject of WO 2011/021041A. Anti-κ and anti-λ assays are also available from a number of other available commercial sources including Siemens AG, which use monoclonal antibodies in comparison with a polyclonal assay produced by The Binding Site Group Limited. Monoclonal based assays may have limited epitope specificity (ref R. J. Lock, Ann Clin Biochem 2013: 1-7) and so have the potential to miss certain clones; this may be further exacerbated by the presence of multimeric monoclonal free light chains.

The analyte is typically one which forms multimers. It may, for example, be a protein. The analyte itself is typically not broken down by the separating agent. The separating agent typically breaks bonds, such as disulphide or hydrogen bonds between analyte molecules but does not substantially cause the analyte molecule to be degraded. Hence, the amino acid chain of a protein would not be broken by the separating agent.

The separating agent typically causes the separation of monomers of the analyte without substantially degrading the monomers themselves, may for example be a reducing agent, chaotropic agent or a detergent. Reducing agents, such as cysteine, glutathione, tris(2-carboxyethyl)phosphine (TCEP), β-mercaptoethanol (2-ME) β-mercaptoethanesulfonic acid, β-mercaptoethylamine (cysteamine; 2-MEA), dithiothreitol (DTT) and dithioerythritol (DTE) reduce disulphide bonds between, for example, individual multimeric light chains. Chaotropic agents are molecules in water solution that can disrupt the hydrogen bonding that work between water molecules. This can affect the stability of water molecules in the solutions by weakening the hydrophobic effect. Different compounds have different chaotropic effects. Compounds include ethanol which interferes with non-covalent intramolecular forces, salts which can affect the charges and prevent stabilisation of salt bridges. Chaotropic agents include butanol, ethanol, guanidinuim chloride, lithium perchlorate, lithium acetate, magnesium chloride, thenol, propranol, thiourea and urea. These may be used because some multimers are produced by intramolecular bonding, rather than for example, disulphide bonding. Similarly, detergents or surfactants may also be used.

Reducing agents have been found to be especially useful. Accordingly, typically a reducing agent is used. This may be further enhanced by the optional addition of a chaotropic agent or detergent/surfactant.

The problem with previous attempts to separate multimeric analyte, such as free light chain, is that large amounts of the disrupting agent have been used. That can affect the analyte specific binding agent. Accordingly, selecting the concentration of the separating agent to allow the separating agent to separate the multimeric analyte without substantially affecting the analyte-specific binding agent, or indeed affecting intact immunoglobulins where intact immunoglobulins are present in the sample, improves the way that the assay works.

Typically, the separating agent is incubated with the sample for 5 seconds to 20 minutes, especially 30 seconds to 5 minutes prior to quenching or adding the FLC binding agent.

Typically the concentration of the separating agent used to disrupt the multimeric analyte is less than 100 mM, less than 50 mM, less than 30 mM, less than 25 mM, typically more than 1 mM, more than 2 mM, more than 5 mM, more than 10 mM, most typically 6 mM, 12 mM, 12.5 mM or 15 mM.

Time and concentration are typically related. A shorter time is typically used with a higher concentration and vice versa.

Treating the calibrator used to produce a calibration curve also improves the accuracy of the assay. This ensures that the calibration curve obtained by binding the analyte-specific binding agent to predetermined amounts of analyte under substantially the same conditions as the assay being performed on the sample, reduces the effect of the separation step on the accuracy of the amount of multimeric analyte detected.

The calibrator may be monoclonal, or typically polyclonal, free light chain.

The amount of multimeric analyte detected is typically the separated multimeric analyte plus any monomeric analyte which may also have been present within the sample. With free light chains, for example, not all of the free light chain is in multimeric form, but there will typically be some monomeric free light chain also available. It is the sum total of the separated multimeric analyte, plus monomeric analyte, plus any untreated multimeric analyte which may be present, which is detected by the assay. Typically substantially all of the multimeric analyte is converted into monomeric analyte.

Typically the sample is a biological fluid, such as blood, serum, plasma, saliva, urine, cerebrospinal fluid (CSF), especially blood, serum or plasma.

A quenching agent may be used to substantially stop the interaction of the separating agent with the multimeric analyte. For example, the quenching agent is typically added to the monomeric analyte after the multimeric analyte has been treated with the separating agent, but before binding the analyte to the analyte-specific binding agent. The quenching agent typically decreases the activity of the separating agent, for example by binding to or reacting with unreacted separating agent left over from the reaction of the separating agent with the multimeric analyte. For example, where the separating agent is a reducing agent, the quenching agent may be an iodoaceteamide, polyethyleic glycol maleimide (PEG maleimide), or methyl sulfonyl benzothiazole (MSBT). Simply diluting the reaction mixture with a diluent, such as a buffer solution, may also be used to decrease and substantially inhibit the effects of the separating agent, such as for example a detergent or chaotropic agent.

Methods of the invention may be used to determine an amount of the multimeric analyte as described above and may be used in the screening, diagnosis, monitoring or diagnosis of a disease in a patient. The assay may also be used, for example, in the detection of analytes in other situations, such as the soil, plants or indeed animals. Typically the disease is a B-cell associated disease. Typically the disease is selected from smouldering multiple myeloma, intact immunoglobulin myeloma, light chain myeloma, non-secretory myeloma, an MGUS, AL amyloidosis, Waldenström's macroglobulinaemia, Hodgkin's lymphoma, follicular centre cell lymphoma, chronic lymphocytic leukaemia, mantle cell lymphoma, pre-B cell leukaemia or acute lymphoblastic leukaemia.

The method may be used in, for example, a nephelometric, turbidimetric, flow cytometric, lateral flow, immunofixation electrophoresis (IFE), ELISA assay or indeed may comprise the use of a biosensor comprising the analyte-specific binding agent immobilised thereon. They may be laboratory based or point of care assays.

On flow cytometry, lateral flow, IFE and ELISA assays the sample may be treated by the separating agent and optionally a quenching agent, for example, prior to adding to the assay.

Lateral flow assay, which are also known as lateral flow immunochromatographic assay, are simple devices intended to detect the presence or absence of a target analyte in a sample without the need for specialised and costly equipment. Typically these tests are used for medical diagnostics either for home testing, point of care testing or laboratory use. It utilises a capillary bed, such as a porous paper or sintered polymer. This transports the sample which migrates to an element in which the manufacturer has stored, for example, antibody which binds to analyte within the sample. The sample then migrates to a detection layer where the presence or absence of the sample is detected. Such lateral flow devices are generally known in the art.

ELISA, for example uses antibodies to detect specific antigens. One or more of the antibodies used in the assay may be labeled with an enzyme capable of converting a substrate into a detectable analyte. Such enzymes include horseradish peroxidase, alkaline phosphatase and other enzymes known in the art. Alternatively, other detectable tags or labels may be used instead of, or together with, the enzymes. These include radioisotopes, a wide range of coloured and fluorescent labels known in the art, including fluorescein, Alexa Fluor™ fluorescent dye (Molecular Probes, Inc., Eugene Oregon), Oregon Green™ fluorescent dye (Molecular Probes, Inc.), BODIPY™ fluorescent dye (Molecular Probes, Inc.), rhodamine red, Cascade Blue™ fluorescent dye (Molecular Probes, Inc.), Marina Blue™ fluorescent dye (Molecular Probes, Inc.), Pacific Blue, Cascade Yellow, gold; and conjugates such as biotin (available from, for example, Invitrogen Ltd, United Kingdom). Dye sols, metallic sols, chemiluminescent labels or coloured latex may also be used. One or more of these labels may be used in the ELISA assays according to the various inventions described herein, or alternatively in the other assays, labeled antibodies or kits described herein.

The construction of ELISA-type assays is itself well known in the art. For example, a "binding antibody" specific for the FLC is immobilised on a substrate. The "binding antibody" may be immobilised onto the substrate by methods which are well known in the art. FLC in the sample are bound by the "binding antibody" which binds the FLC to the substrate via the "binding antibody".

Unbound immunoglobulins may be washed away.

In ELISA assays the presence of bound immunoglobulins may be determined by using a labeled "detecting antibody" specific to a different part of the FLC of interest than the binding antibody.

Flow cytometry may be used to detect the binding of the FLC of interest. This technique is well known in the art for, e.g. cell sorting. However, it can also be used to detect labeled particles, such as beads, and to measure their size. Numerous text books describe flow cytometry, such as Practical Flow Cytometry, 3rd Ed. (1994), H. Shapiro, Alan R. Liss, New York, and Flow Cytometry, First Principles (2nd Ed.) 2001, A. L. Given, Wiley Liss.

One of the binding antibodies, such as the antibody specific for FLC, is bound to a bead, such as a polystyrene or latex bead. The beads are mixed with the sample and the second detecting antibody. The detecting antibody is preferably labeled with a detectable label, which binds the FLC to be detected in the sample. This results in a labeled bead when the FLC to be assayed is present.

Labeled beads may then be detected via flow cytometry. Different labels, such as different fluorescent labels may be used for, for example, the anti-free λ and anti-free κ antibodies. Other antibodies specific for other analytes described herein may also be used in this or other assays described herein to allow the detection of those analytes. This allows the amount of each type of FLC bound to be determined simultaneously or the presence of other analytes to be determined.

Alternatively, or additionally, different sized beads may be used for different antibodies, for example for different marker specific antibodies. Flow cytometry can distinguish between different sized beads and hence can rapidly determine the amount of each FLC or other analyte in a sample.

An alternative method uses the antibodies bound to, for example, fluorescently labeled beads such as commercially available Luminex™ micro-sphere beads. Different beads are used with different antibodies. Different beads are labeled with different fluorophore mixtures, thus allowing different analytes to be determined by the fluorescent wavelength. Luminex™ beads are available from Luminex Corporation, Austin, Texas, United States of America.

Preferably the assay used is a nephelometric or turbidimetric method. Nephelometric and turbidimetric assays for the detection of λ- or κ-FLC are generally known in the art.

The biosensors comprising analyte-specific binding agents, such as antibodies or fragments of antibodies, are generally known in the art. They include, for example, OCTET biosensors of the type generally produced by Forté BIO, and other biosensors manufacturers in the art.

Two or more analytes may be quantified in the sample. For example, λ and κ free light chains may be separately assayed and the two separate amounts identified in the sample then used to identify the κ/λ ratio.

Additionally, one or more further analytes may be utilised. These may include, for example, cancer antigens, bacterial antigen, viral antigens, cholesterol, C-reactive protein, cystatin C, albumin, urea and serum creatinine. These may be determined using analyte-specific binding agents against those analytes, such as antibodies or fragments thereof.

The invention also provides assay kits for use in the methods of the invention. These typically comprise an analyte-specific binding agent and a separating agent to separate at least a portion of the multimeric analyte into a monomeric analyte. Typically, the separating agent and analyte-specific binding agent are combined within a single packaging to produce the kit. The analyte-specific binding agent and separating agent may be as defined above.

The assay kit may also comprise a predetermined amount of the analyte, for example, as a calibrator. This allows the production of a calibration curve for use in the methods of the invention. The assay kit may comprise two or more different antigen-specific binding agents to allow the detection of two or more different analytes, for example, in a multiplex system, as described above.

The analyte-specific binding agent may be attached to a substrate, such as a bead, latex particle, a Luminex bead, a linear flow device (such as a matrix of the device) or the surface of a biosensor.

Typically the antibody is a monoclonal antibody or a polyclonal antibody. FLC may be λ, κ or total FLC.

The invention will now be described by way of example only with reference to the following figures.

Figure 1:
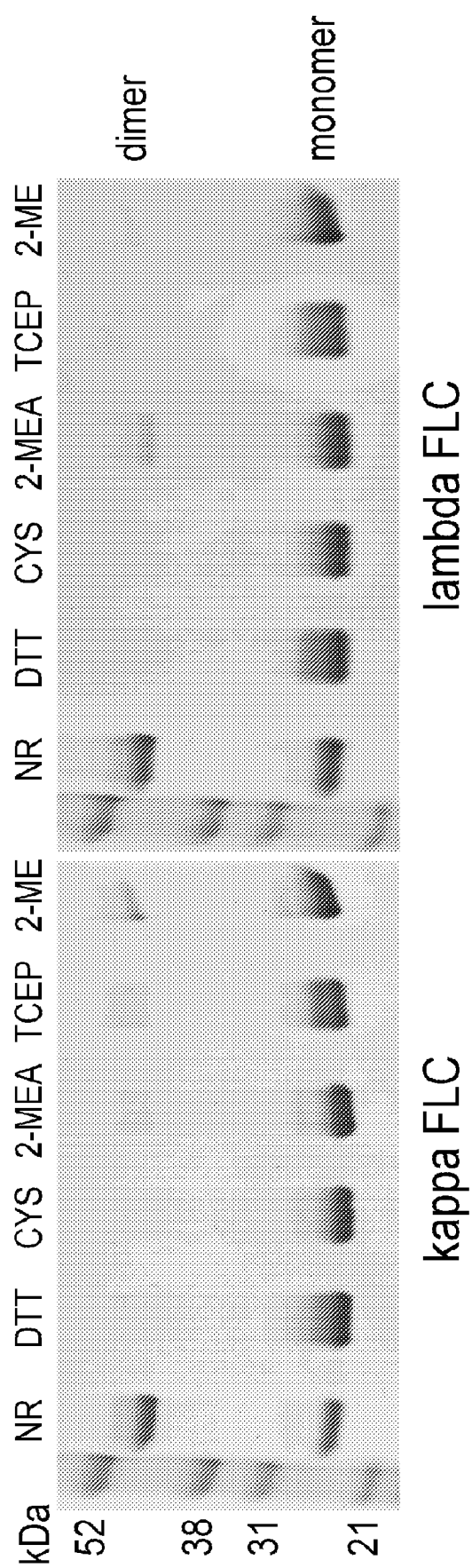
FIG. 1 shows the separation of κ and λ FLC dimers into monomers by the addition of dithiothreitol (DTT, 15 mM), cysteine (CYS, 15 mM), β-mercaptoethylamine (2-MEA, 15 mM), tris(2-carboxyethyl)phosphine (TCEP, 20 mM) and β-mercaptoethanol (2-ME, 25 mM). A mixed monomeric/dimeric population of κ and λ FLC was observed in the absence of reducing agent (NR).

FIG. 1 shows that light chains can be dissociated from dimeric to monomeric form by the addition of low concentrations of mild reducing agents. Light chains were purified to homogeneity. The κ or λ free light chains were then treated with dithiothreitol, cysteine, β-mercaptoethylamine, tris(2-carboxyethyl)phosphine and β-mercaptoethanol. Reactions were then stopped by the addition of excess iodoacetamide and the reactions analysed by SDS-PAGE and stained with Coomassie Blue.

The figure shows that the larger dimeric free light chains were separated into monomeric free light chains by the addition of the reducing agents.

Figure 2A:
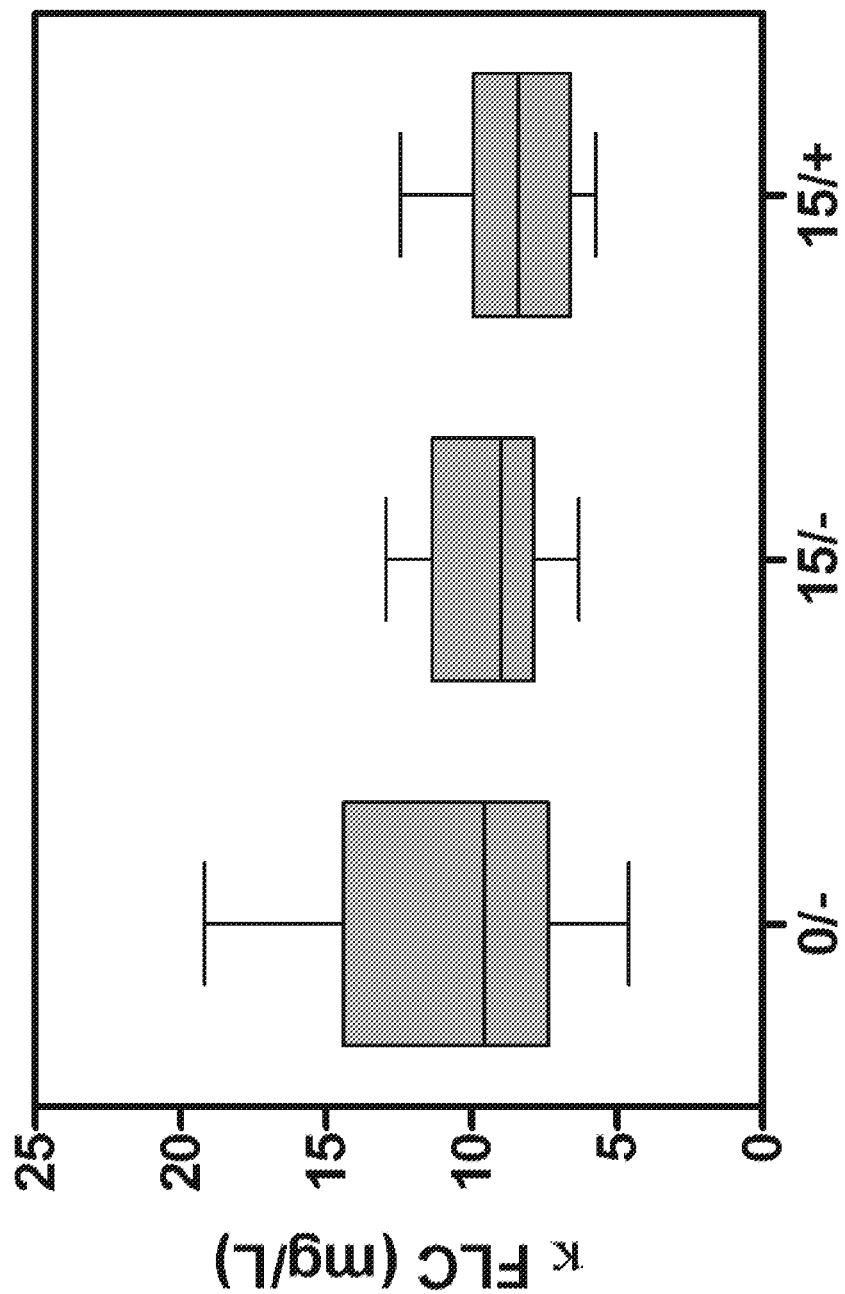
FIG. 2 shows the detection of κ (a) and λ (b) FLC in normal healthy serum (0/−) compared to samples treated with 15 mM cysteine (15/−) and 15 mM cysteine followed by quenching with iodoacetamide (15/+) prior to assaying for free light chains.
Figure 2B:
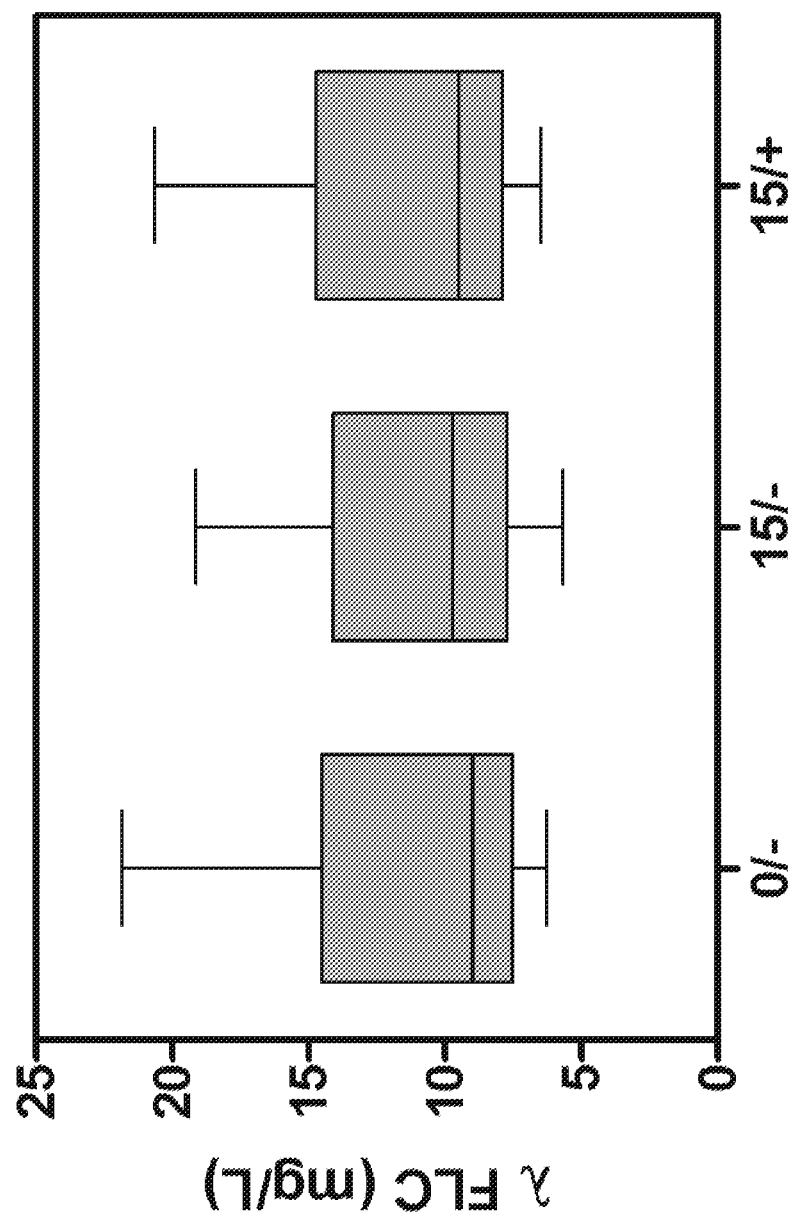

FIG. 2 shows the effect of mild reducing conditions on the κ FLC and λ FLC values from 20 normal human serum samples analysed using Freelite™. Calibrator controls were also treated the same way with reducing agent and IAA as appropriate. Irrespective of the addition of iodoacetamide (IAA), samples treated with 15 mM cysteine prior to being assayed by Freelite™ remained within the normal 95$^{th}$ percentile range for κ and λ FLC (κ, 3.3-19.4 mg/L; λ, 5.71-26.3 mg/L). Pre-treatment with 15 mM cysteine was also shown to improve the variability of the measurements and indeed reduce the amount of deviation from the observed mean value.

Figure 3:
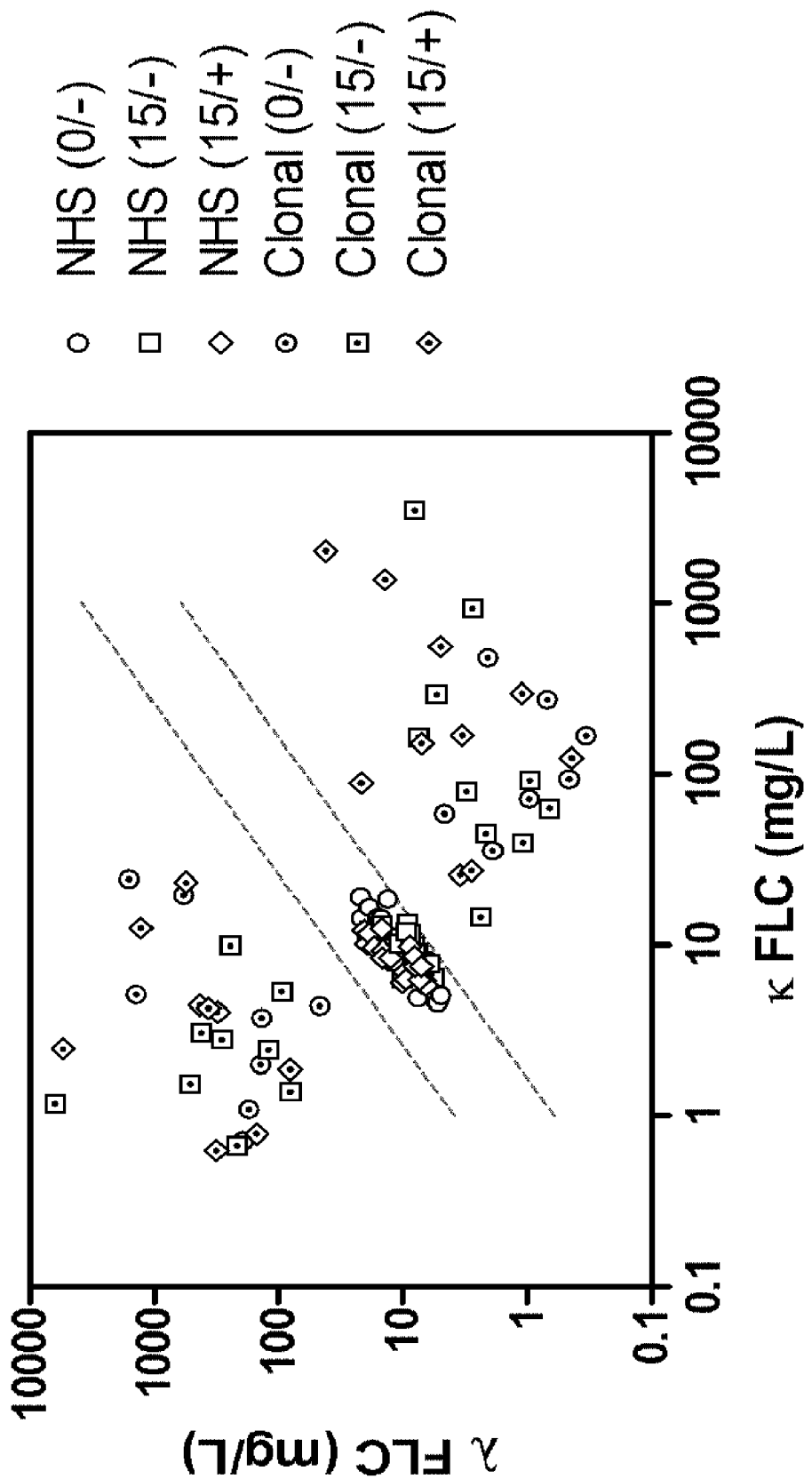
FIG. 3 shows a scatter plot of κ FLC versus λ FLC values for normal and myeloma sera treated with 15 mM cysteine (15/−) and 15 mM cysteine followed by quenching with iodoacetamide (15/+) prior to assaying for free light chains. The diagonal tram lines represent the extremities of the normal range.

FIG. 3 shows the distribution of κ/λ ratios for normal human sera and myeloma sera treated with mild reducing conditions (15 mM cysteine with and without additional IAA), prior to assaying for κ and λ FLC using Freelite™. Under each experimental condition, all normal human sera remain within the normal κ/λ ratio range (diagonal tramlines) and all sera containing monoclonal protein remain outside of the normal κ/λ ratio range. The data indicates that the presence of predominantly monomer free light chains in clinical samples does not alter the clinical interpretation of the assay results. Under each experimental condition, all normal human sera remain within the normal kappa/lambda ratio range (diagonal tramlines) and all sera containing monoclonal protein remain outside of the normal kappa/lambda ratio range.

Figure 4A:
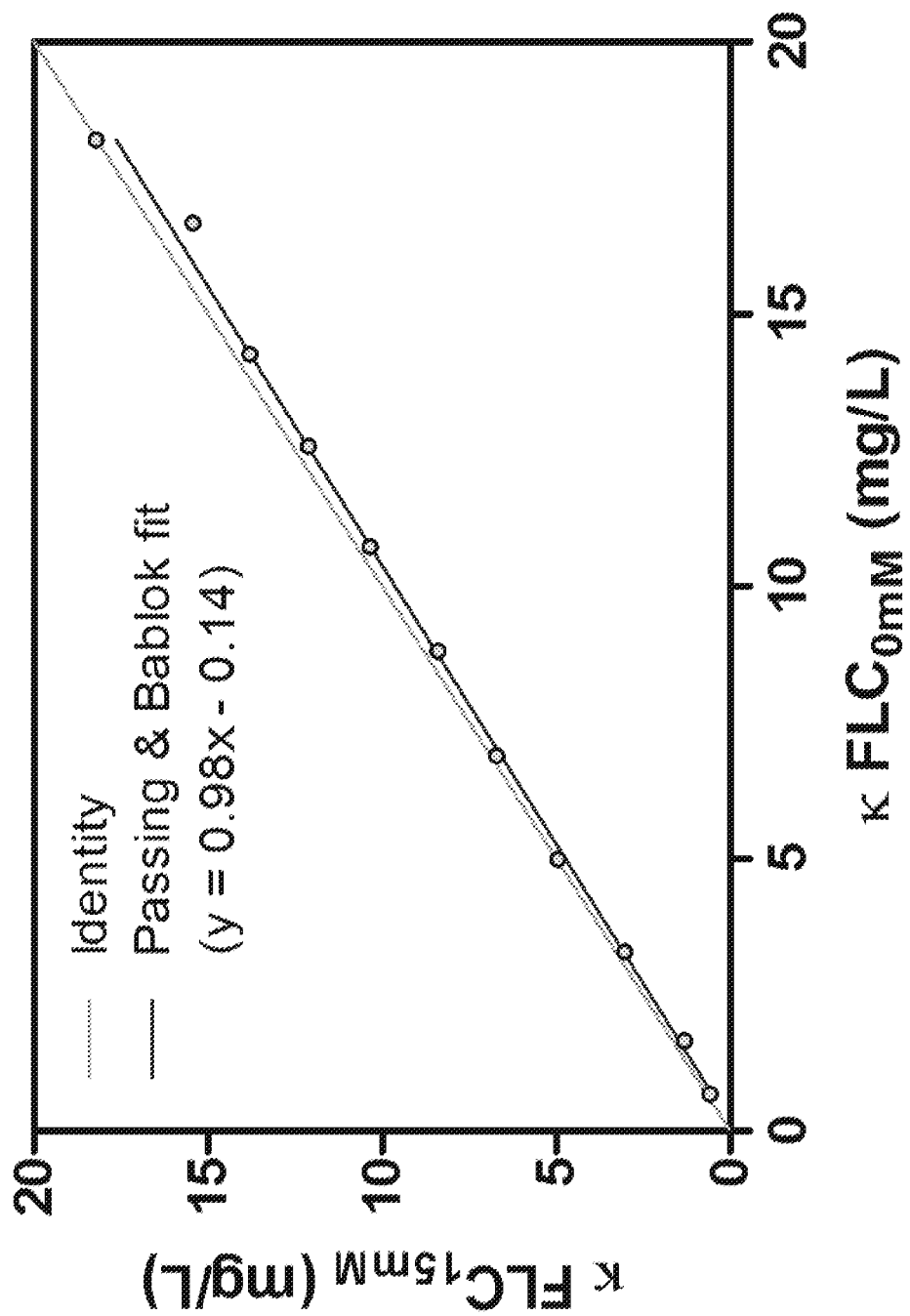
FIG. 4 shows the κ (FIG. 4a) and λ (FIG. 4b) values obtained by Freelite™ assay for serially diluted human serum pre-treated with 0 mM or 15 mM cysteine.
Figure 4B:
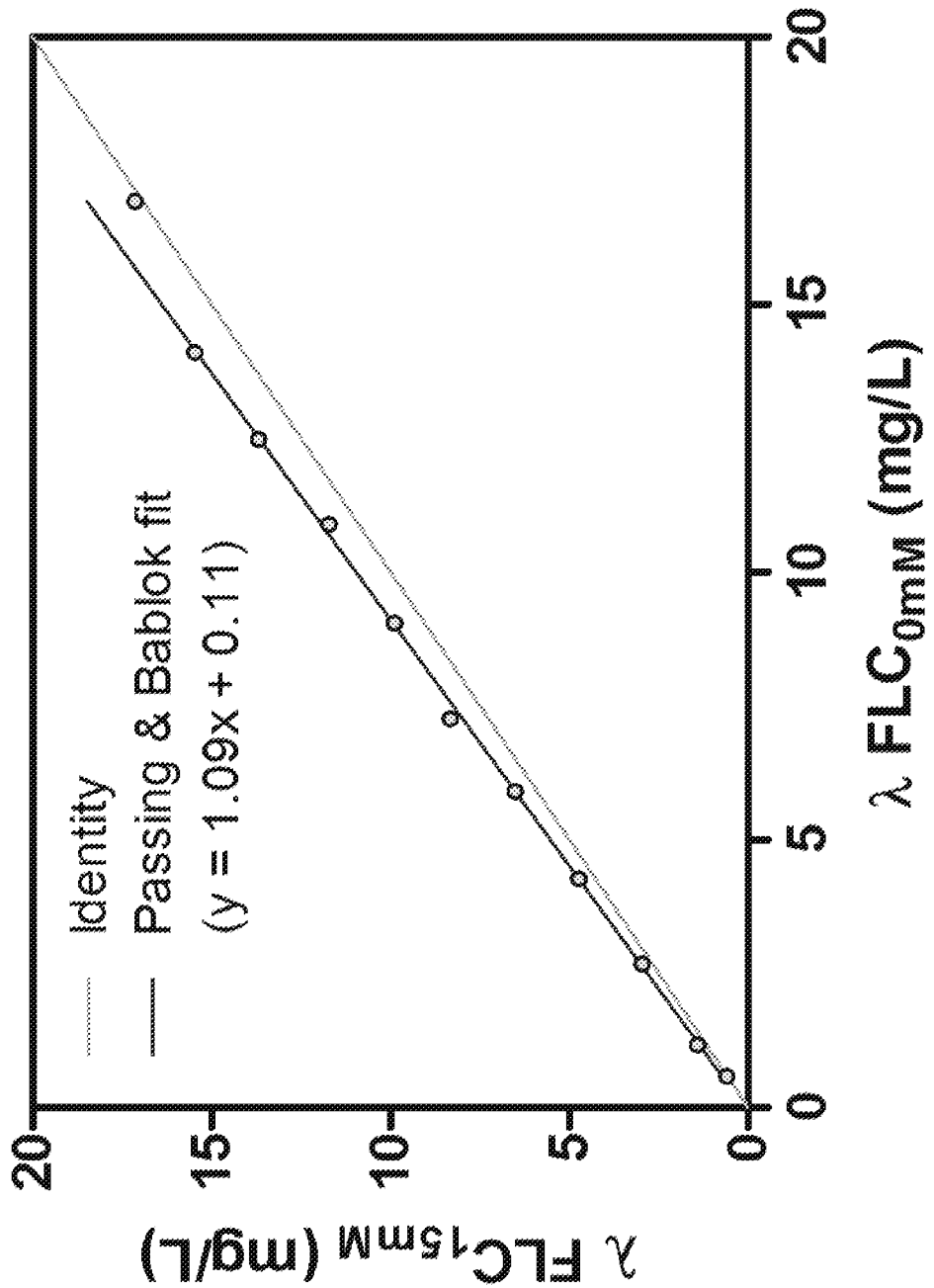

FIG. 4A and FIG. 4B show that free light chain values (4a, κ; 4b, λ) obtained by the Freelite™ assay remain in good agreement following pre-treatment of serially diluted human serum with 0 mM or 15 mM cysteine. Undiluted serum, corresponding to the highest FLC values shown, contained polyclonal IgG, IgA and IgM at 9.45, 2.62 and 0.47 g/L, respectively. Passing and Bablok regression analysis demonstrated good analytical agreement between each treatment for both κ and λ light chains. The absence of systematic bias and the good linearity indicates that there was no significant release of light chain from intact immunoglobulins.

Figure 5:
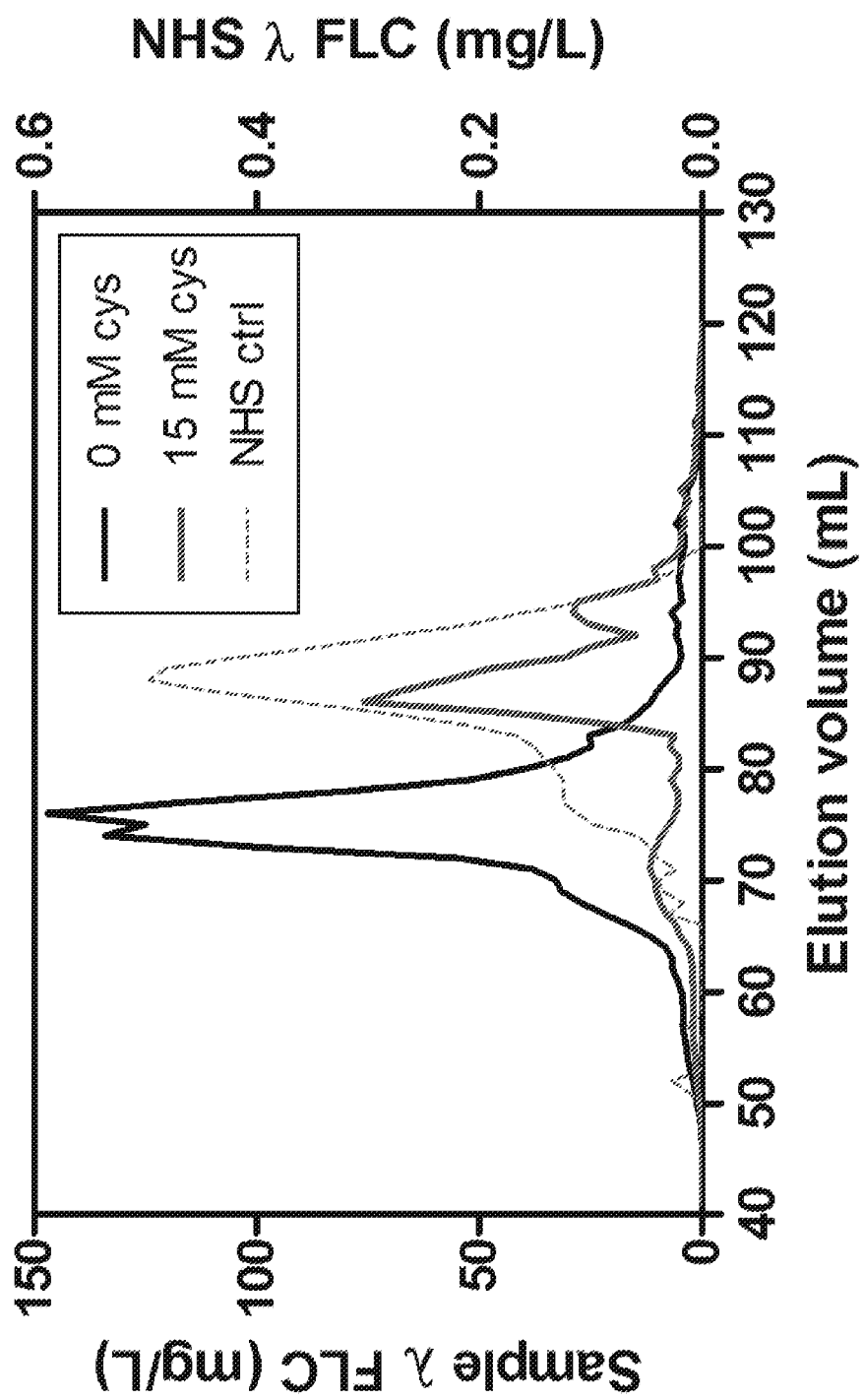
FIG. 5 shows the effect of 15 mM cysteine on FLC polymerisation as measured by S200 gel filtration and free light chain assay.

FIG. 5 shows the effect of the addition of 15 mM cysteine on polymerised λ FLC serum. The left-hand peak shows a polymerised monoclonal FLC sample from a multiple myeloma patient. The addition of 15 mM cysteine is shown to shift the main peak, indicating that polymerised λ free light chains have been converted into a mixture of dimer and monomer. The peak therefore overlaps with the normal free light chains found in normal serum (the dotted peak). This shows that for this sample the lower molecular weight forms have less immunoreactivity with Freelite reagent.

Table 1 shows that the reported value for the polymerised λ FLC sample, shown in FIG. 5, was decreased by the addition of 15 mM cysteine prior to assaying with Freelite™.

TABLE 1

| Cysteine (mM) | λ FLC (mg/L) |
|---|---|
| 0 | 12009 |
| 15 | 5847 |

The invention claimed is:

1. A method of preparing a biological sample for quantification of a multimeric analyte, comprising:
   (i) pre-treating the biological sample with a separating agent for 5 seconds to 20 minutes to convert at least a portion of the multimeric analyte into a monomeric analyte; and
   (ii) binding the monomeric analyte to an anti-monomeric analyte-specific antibody, or anti-monomeric analyte-specific binding fragment thereof, said antibody or fragment comprising means for binding the monomeric analyte;

wherein the separating agent is selected from the group consisting of: cysteine, tris (2-carboxyethyl) phosphine (TCEP), β-mercaptoethanol (2-ME), β-mercaptoethylamine (cysteamine, 2-MEA), and dithiothreitol (DTT), and wherein a concentration of the separating agent is 5 mM to 100 mM;

further wherein the multimeric analyte is a multimeric free light chain (FLC) and the biological sample is a blood, serum, plasma, or cerebrospinal fluid (CSF) sample.

2. The method according to claim 1, wherein the multimeric FLC is a kappa FLC, a lambda FLC, or a total FLC.

3. The method according to claim 1, additionally comprising the step of adding a quenching agent to the monomeric analyte after the multimeric analyte has been treated with the separating agent, but before binding the monomeric analyte to the anti-monomeric analyte-specific antibody or anti-monomeric analyte-specific binding fragment thereof, wherein the quenching agent reduces the activity of the separating agent.

4. The method according to claim 3, wherein the quenching agent is iodoacetamide, polyethyleneglycol (PEG) maleimide, or methylsulfonyl benzothiazole (MSBT).

5. The method according to claim 1, wherein the biological sample is obtained from a patient with a disease selected from a B-cell associated disease, smouldering multiple myeloma, intact immunoglobulin myeloma, light chain myeloma, non-secretory myeloma, monoclonal gammopathies of undetermined significance (MGUS), Amyloid light chain amyloidosis (AL amyloidosis), Waldenström's macroglobulinaemia, Hodgkin's lymphoma, follicular centre cell lymphoma, chronic lymphocytic leukaemia, mantle cell lymphoma, pre-B cell leukaemia or acute lymphoblastic leukaemia.

6. The method according to claim 1, further including quantifying the multimeric analyte by a method selected from the group consisting of: a nephelometric, turbidimetric, flow cytometric, lateral flow, immunofixation electrophoresis (IFE) or enzyme-linked immunosorbent assay (ELISA), or by a method comprising the use of a biosensor comprising an immobilized binding agent.

7. The method according to claim 1, wherein two or more analytes are quantified in the sample.

8. The method according to claim 7, additionally comprising measuring in the sample one or more further analytes selected from a cancer antigen, a bacterial antigen, a viral antigen, cholesterol, C-reactive protein, cystatin C, albumin, urea, and serum creatinine.

9. The method according to claim 1, wherein the method is performed using a kit comprising:
    a monomeric free light chain-specific antibody or a monomeric free light chain-specific fragment thereof each comprising means for binding a monomeric free light chain; and
    a separating agent adapted to convert at least a portion of the multimeric free light into a monomeric free light chain, the separating agent being selected from the group consisting of: cysteine, tris (2-carboxyethyl) phosphine (TCEP), β-mercaptoethanol (2-ME), β-mercaptoethylamine (cysteamine; 2-MEA), and dithiothreitol (DTT), and wherein a concentration of the separating agent is 5 mM to 100 mM.

10. A method of preparing a biological sample for quantification of a multimeric free light chain (FLC), comprising:
  (i) pre-treating the biological sample with a separating agent for 5 seconds to 20 minutes to convert at least a portion of the multimeric FLC into a monomeric FLC; and
  (ii) binding the monomeric FLC to an anti-monomeric FLC-specific antibody or anti-monomeric FLC-specific binding fragment thereof, said antibody or fragment comprising means for binding monomeric FLC;
  wherein the separating agent is selected from the group consisting of: cysteine, tris (2-carboxyethyl) phosphine (TCEP), β-mercaptoethanol (2-ME), β-mercaptoethylamine (cysteamine, 2-MEA), and dithiothreitol (DTT), and wherein a concentration of the separating agent is 5 mM to 100 mM;
  further wherein the biological sample prepared for quantification of the multimeric FLC is a blood, serum, plasma, or cerebrospinal fluid (CSF) sample.

11. The method of claim 10, further including binding the anti-monomeric FLC-specific antibody or anti-monomeric FLC-specific binding fragment thereof to one or more predetermined amounts of a separating agent-treated monomeric FLC.

12. The method according to claim 10, additionally comprising the step of adding a quenching agent to the monomeric FLC after the multimeric FLC has been treated with the separating agent, but before binding the monomeric FLC to the anti-monomeric FLC-specific antibody or anti-monomeric FLC-specific binding fragment thereof, wherein the quenching agent reduces the activity of the separating agent.

13. A method of preparing a biological sample for quantification of a multimeric analyte, comprising: pre-treating the biological sample with a separating agent for 5 seconds to 20 minutes to convert at least a portion of the multimeric analyte into a monomeric analyte,
  wherein the separating agent is selected from cysteine, tris (2-carboxyethyl) phosphine (TCEP), β-mercaptoethanol (2-ME), β-mercaptoethylamine (cysteamine, 2-MEA), and dithiothreitol (DTT), and a concentration of the separating agent is 5 mM to 100 mM;
  further wherein the biological sample prepared for quantification of the multimeric analyte is a blood, serum, plasma, or cerebrospinal fluid (CSF) sample.

14. The method according to claim 13, wherein the multimeric analyte FLC is a kappa FLC, a lambda FLC, or a total FLC.

15. The method according to claim 13, additionally comprising the step of adding a quenching agent to the monomeric analyte after the multimeric analyte has been treated with the separating agent.

16. The method according to claim 15, wherein the quenching agent is iodoacetamide, polyethyleneglycol (PEG) maleimide, or methylsulfonyl benzothiazole (MSBT).

17. The method according to claim 13, wherein the biological sample is obtained from a patient with a disease selected from a B-cell associated disease, smouldering multiple myeloma, intact immunoglobulin myeloma, light chain myeloma, non-secretory myeloma, monoclonal gammopathies of undetermined significance (MGUS), Amyloid light chain amyloidosis (AL amyloidosis), Waldenström's macroglobulinaemia, Hodgkin's lymphoma, follicular centre cell lymphoma, chronic lymphocytic leukaemia, mantle cell lymphoma, pre-B cell leukaemia or acute lymphoblastic leukaemia.

18. The method according to claim 13, further including quantifying the multimeric analyte by a method selected from the group consisting of: a nephelometric, turbidimetric, flow cytometric, lateral flow, immunofixation electrophoresis (IFE) or enzyme linked immunosorbent assay (ELISA), or by a method comprising the use of a biosensor comprising an immobilized binding agent.

19. The method according to claim 13, wherein two or more analytes are quantified in the sample.

20. The method according to claim 19, additionally comprising measuring in the sample one or more further analytes selected from a cancer antigen, a bacterial antigen, a viral antigen, cholesterol, C-reactive protein, cystatin C, albumin, urea, and serum creatinine.

\* \* \* \* \*